United States Patent
Yuan et al.

(10) Patent No.: US 8,362,256 B2
(45) Date of Patent: Jan. 29, 2013

(54) SALTS OF N-[4-(1-CYANOCYCLOPENTYL) PHENYL]-2-(4-PYRIDYLMETHYL)AMINO-3-PYRIDINECARBOXAMIDE

(75) Inventors: Kaihong Yuan, Jiangsu (CN); Piaoyang Sun, Jiangsu (CN); Yunshu Zhou, Jiangsu (CN); Yongjiang Chen, Jiangsu (CN)

(73) Assignee: Jiangsu Hengrui Medicine Co. Ltd. (CN)

( * ) Notice: Subject to any disclaimer, the term of this patent is extended or adjusted under 35 U.S.C. 154(b) by 0 days.

(21) Appl. No.: 13/063,850

(22) PCT Filed: Jun. 11, 2009

(86) PCT No.: PCT/CN2009/072239
§ 371 (c)(1), (2), (4) Date: Mar. 14, 2011

(87) PCT Pub. No.: WO2010/031266
PCT Pub. Date: Mar. 25, 2010

(65) Prior Publication Data
US 2011/0184023 A1    Jul. 28, 2011

(30) Foreign Application Priority Data
Sep. 16, 2008 (CN) .......................... 2008 1 0149651

(51) Int. Cl.
*C07D 213/79* (2006.01)
*A61K 31/44* (2006.01)
(52) U.S. Cl. ........................................ 546/263; 514/332
(58) Field of Classification Search ........................ None
See application file for complete search history.

(56) References Cited

U.S. PATENT DOCUMENTS
7,129,252 B2 * 10/2006 Chen .............................. 514/332
2004/0259916 A1 * 12/2004 Chen .............................. 514/340

FOREIGN PATENT DOCUMENTS
CN    1502608 A    6/2004
WO    WO 2004/013102 A1    2/2004

OTHER PUBLICATIONS

Berge, SM. et al. Pharmaceutical Salts. J. Pharm. Sci. 1977, vol. 66(1), p. 1-19.*
Freshney, RI. Culture of Animal Cells: A Manual of Basic Technique. John Wiley and Sons. 2005, 5th Ed., p. 8.*
Dermer, GB. Another Anniversary for the War on Cancer. Bio/Technology. 1994, vol. 12, p. 320.*
Engel, GL. et al. Slat form selection and characterization of LY333531 mesylate monohydrate. International Journal of Pharmaceutics. 2000, vol. 198, p. 239-240.*
Israel Posner et al., "Kinetic Model of the Epidermal Growth Factor (EGF) Receptor Tyrosine Kinase and a Possible Mechanism of Its Activation by EGF*," J. Biol. CHem., Oct. 1992, vol. 267, Issue 29, pp. 20638-20647.
Jeanette M. Wood et al., "PTK787/ZK 222584, a Novel and Potent Inhibitor of Vascular Endothelial Growth Factor Receptor Tyrosine Kinases, Impairs Vascular Endothelial Growth Factor-induced Responses and Tumor Growth after Oral Administration," Cancer Research 60, Apr. 15, 2000, pp. 2178-2189.

* cited by examiner

*Primary Examiner* — Janet Andres
*Assistant Examiner* — Heidi Reese
(74) *Attorney, Agent, or Firm* — Brinks Hofer Gilson & Lione; Ryan L. Marshall

(57) ABSTRACT

The present invention relates to the salts of N-[4-(1-cyanocyclopentyl)phenyl]-2-(4-pyridylmethyl)amino-3-pyridine carboxamide, especially hydrochloride and mesylate thereof, and the use of said salts in the preparation of an antineoplastic medicament.

4 Claims, 3 Drawing Sheets

Figure 1. Efficacy of mesylate of compound A, PTK787 on human colon cancer Ls174t transplanted in nude mice Figure 2. Efficacy of mesylate of compound A, PTK787 on human colon cancer HT-29 transplanted in nude mice

SALTS OF N-[4-(1-CYANOCYCLOPENTYL) PHENYL]-2-(4-PYRIDYLMETHYL)AMINO-3-PYRIDINECARBOXAMIDE

REFERENCE TO EARLIER FILED APPLICATIONS

The present application is the national phase application of PCT Application No. PCT/CN2009/072239, filed Jun. 11, 2009, which claims priority to Chinese Patent Application No. 200810149651.1, filed Sep. 16, 2008, the entireties of both of which are hereby incorporated by reference.

FIELD OF THE INVENTION

The present invention relates to the pharmaceutically acceptable salts of N-[4-(1-cyanocyclopentyl)phenyl]-2-(4-pyridylmethyl)amino-3-pyridine carboxamide.

BACKGROUND OF THE INVENTION

Tumor angiogenesis plays a critical role in the malignant tumor growth and metastasis. When tumors grow beyond 1 mm$^3$, angiogenesis or generation of vascular arborizations by budding from existing vessels is necessary to provide enough blood for the survival of tumor cells. The growth speed and tendency of metastasis of tumors are associated with the level of neovascularization factors and the quantity of nascent microvessels. Since the hypothesis "anti-angiogenesis therapy" was put forward by Folkman in early 1970s, people have made considerable progress in this field, and inhibiting angiogenesis of tumors has been universally accepted as a new anticancer strategy.

Tyrosine kinase vascular endothelial growth factor (VEGF) and its receptor (VEGFR) play significantly important roles in angiogenesis of tumors, and they are both important targets in blocking angiogenesis of tumors. Vascular endothelial growth factor (VEGF) is the foremost factor in vivo promoting the angiogenesis. The binding of VEGF with vascular endothelial growth factor receptor (VEGFR) in endothelial cells leads to various reactions of angiogenesis, such as cells proliferation, cells metastasis, the increase of vascular permeability, and the move of endothelial cells precursors out of marrow. VEGFR family comprises VEGFR1 (Flt-1), VEGFR2 (KDR/Flk-1) and VEGFR3 (Flt-4). Promotion of the angiogenesis is mainly mediated by the bonded VEGF and VEGFR2 (KDR/Flk-1). Numerous human tumors exhibit high VEGFR levels. Currently, more than 40 medicaments capable of inhibiting angiogenesis are in the clinical trial, such as monoclonal antibodies of VEGF and its receptor (VEGFR), and small molecular inhibitors of VEGFR tyrosine kinase. VEGF monoclonal antibody Avastin, which had been developing by Genetech for more than ten years, was approved for marketing in 2004. The efficacy of Avastin in combination with other medicaments on colon cancer, lung cancer and breast cancer has proved that the mechanism of Avastin as an anti-VEGF drug is feasible. Avastin also made outstanding contributions to the mechanism of anti-angiogenesis as an anti-cancer target.

The most remarkable drugs of small molecular VEGFR inhibitors in recent years include VEGFR inhibitor Vatalanib (PTK787) for the treatment of colon cancer developed by Novartis/Schering, and VEGFR and epidermal growth factor receptor (EGFR) double-target inhibitor Zactima (ZD-6474) for the treatment of relapsed/refractory non-small cell lung cancer developed by Astrazeneca. VEGF inhibitors gradually become new non-cytotoxic anticancer drugs with good application prospects. Compared with traditional cytotoxic drugs which inhibit the growth of tumors, angiogenesis targeting drugs are more specific and less toxic as well as helpful to overcome the drug resistance of tumors and can be used for the treatment of various tumors.

N-[4-(1-cyanocyclopentyl)phenyl]-2-(4-pyridylmethyl) amino-3-pyridine carboxamide (hereinafter referred to as "compound A") is a new generation of tyrosine kinase inhibitor, the compound has the formula (I):

Formula (I):

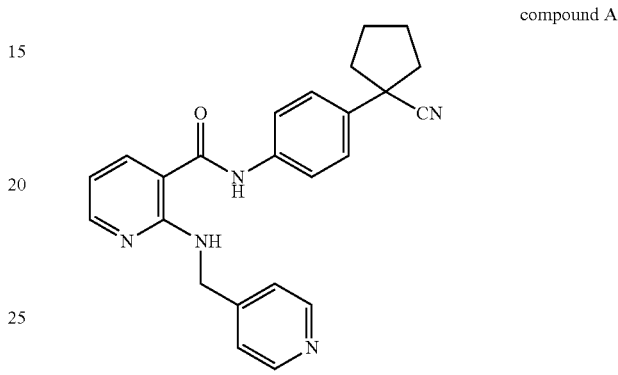

compound A

The above-mentioned compound is recorded in Chinese patent application No. 02138671.4, the content of which is herein incorporated by reference in its entirety. It has been found that compound A has very strong selective inhibition on VEGFR-2 in the enzyme level tests of tyrosine kinase receptors in different laboratories, IC$_{50}$ of which was about 1 nM. In addition, it has certain selective inhibition activity on kinases Ret, VEGFR-1, PDGFR-β, c-kit, cSRC and so on. Pharmacodynamics research of human tumor transplanted in nude mice has found that the efficacy of compound A on colon cancer Ls174t transplanted in nude mice was distinctly better than PTK787; and the efficacy of compound A was improved when it was used in combination with oxaliplatin while the toxicity of which was not increased. Whether used alone or in combination, the efficacy of compound A was better than PTK787. It has also been found that the efficacy of compound A on non-small cell lung cancer A549 transplanted in nude mice was distinctly better than PTK787, the maximum efficacy of which was equivalent to ZD6474 at a customary dose. In the aspect of toxicity, compound A was well tolerated at the maximum dose of 400 mg/kg by nude mice.

However, during the research of the drug, it was found that N-[4-(1-cyanocyclopentyl)phenyl]-2-(4-pyridylmethyl) amino-3-pyridine carboxamide was not satisfying in some aspects, e.g. stability and bioavailability.

SUMMARY OF THE INVENTION

Through protracted efforts, the inventors found that the problems such as stability and bioavailability would be solved by making N-[4-(1-cyanocyclopentyl)phenyl]-2-(4-pyridylmethyl)amino-3-pyridine carboxamide into corresponding pharmaceutically acceptable salts.

In one aspect, the present invention relates to the pharmaceutically acceptable salts of N-[4-(1-cyanocyclopentyl)phenyl]-2-(4-pyridylmethyl)amino-3-pyridine carboxamide, wherein said pharmaceutically acceptable salts are conventional inorganic salts or organic salts in the art. Further, said inorganic salt is preferably selected from the group consisting of hydrochloride salt, hydrobromide salt, sulphate salt, nitrate salt, and phosphate salt, and said organic salt is preferably selected from the group consisting of mesylate salt, maleate salt, tartrate salt, succinate salt, acetate salt, trifluoroacetate salt, fumarate salt, citrate salt, benzene sulfonate salt, benzoate salt, naphthalene sulfonate salt, lactate salt, and malate salt. Particularly preferred pharmaceutically acceptable salts are mesylate salt and hydrobromide salt which are more advantageous in stability, character and bioavailability than other salts.

In another aspect, the present invention relates to a process for preparing pharmaceutically acceptable salts of N-[4-(1-cyanocyclopentyl)phenyl]-2-(4-pyridylmethyl)amino-3-pyridine carboxamide, which is the customary salification method in the art.

In the third aspect, the present invention relates to a pharmaceutical composition comprising therapeutically effective amount of pharmaceutically acceptable salts of N-[4-(1-cyanocyclopentyl)phenyl]-2-(4-pyridylmethyl)amino-3-pyridine carboxamide, which may further comprise one or more pharmaceutically acceptable carriers.

In the fourth aspect, the present invention relates to the use of pharmaceutically acceptable salts of N-[4-(1-cyanocyclopentyl)phenyl]-2-(4-pyridylmethyl)amino-3-pyridine carboxamide in the preparation of anti-tumor drugs.

DETAILED DESCRIPTION OF THE INVENTION

Figure 1:
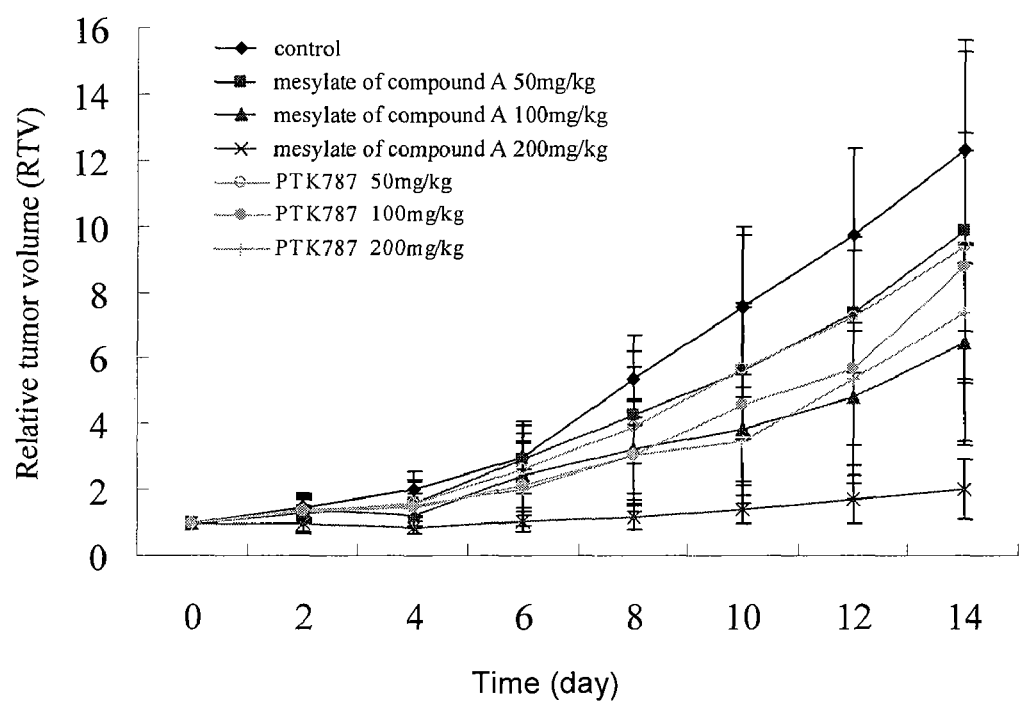
FIG. 1: The efficacy of the mesylate of compound A and PTK787 on human colon cancer Ls174t transplanted in nude mice.
Figure 2:
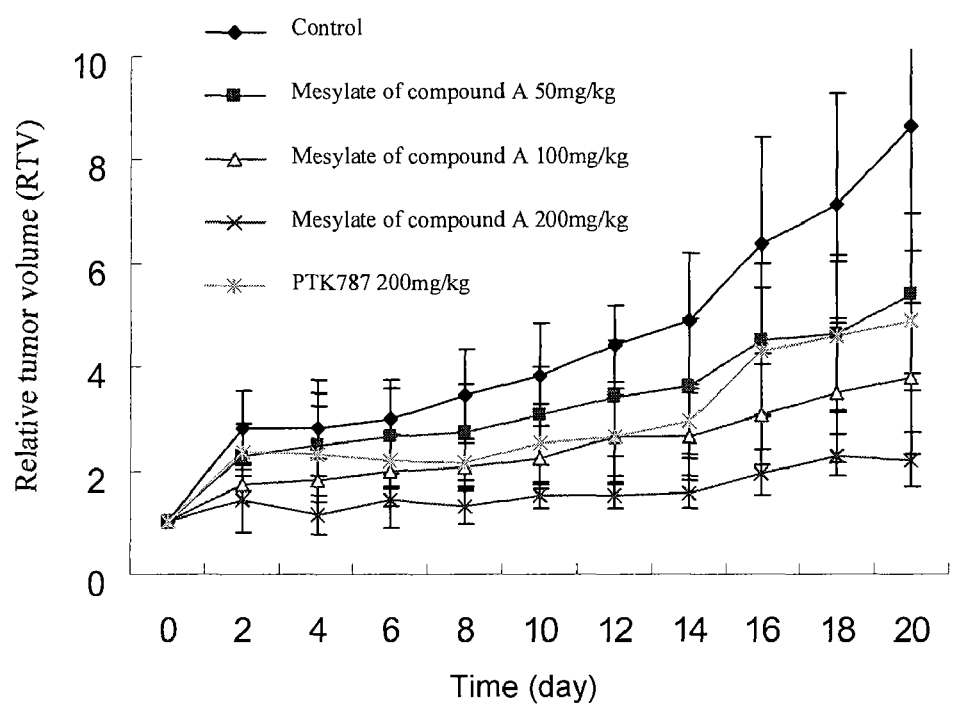
FIG. 2: The efficacy of the mesylate of compound A and PTK787 on human colon cancer HT-29 transplanted in nude mice.

1. Preparation of Pharmaceutically Acceptable Salts of Compound A

Example 1 for Preparation

Preparation of Hydrochloride of Compound A 5.049 g of compound A (12.7 mmol) was suspended in 120 mL of ethanol, 23.89 mL of hydrochloric acid standard solution (0.5322 mol/L) was added dropwise, and the mixture was heated to reflux until a clear solution was obtained (hot filtering may be carried out if any insoluble matter exists). After cooling to the room temperature (23° C.), crystals precipitated from the solution. The resulting mixture was filtered, and the filter cake was washed with ethanol (20 mL×2), transferred to a vacuum drying oven ($CaCl_2$) and filtered by pump for 5 hours at 80° C. to give 3.619 g (65.7%) of hydrochloride of compound A. Melting range: 200~202.5° C., water content 5.1% and solvent residue 0.025%.

Example 2 for Preparation

Preparation of Sulfate of Compound A 3.092 g of compound A (7.778 mmol) was suspended in 120 mL of ethanol, 14.89 mL (7.793 mmol) of sulfuric acid standard solution (0.5234 mol/L) was added dropwise, and the mixture was heated to reflux until a clear solution was obtained (hot filtering may be carried out if any insoluble matters existed). The mixture was concentrated to 100 mL under reduced pressure. After cooling to the room temperature (23° C.), crystals precipitated from the solution. The resulting mixture was filtered, and the filter cake was washed with ethanol (8 mL×2), transferred to vacuum drying oven ($CaCl_2$) and filtered by pump for 5 hours at 80° C. to give 2.662 g (yield 57.7% based on free base content) of sulfate of compound A. Melting range: 199.5~230° C. (not completely melted).

Example 3 for Preparation

Preparation of Phosphate of Compound A

A mixture of 1.910 g of compound A (4.805 mmol), 225 mL of ethanol and 9.29 mL (4.803 mmol) of phosphoric acid standard solution (0.5008 mol/L) was heated to reflux. After 4 hours, solid matters were completely dissolved. Then the mixture was allowed to cool to the room temperature (25° C.), and crystals precipitated from the solution. The resulting mixture was filtered, and the filter cake was washed with ethanol (5 mL×2), transferred to a vacuum drying oven ($CaCl_2$) and filtered by pump for 6 hours at 80° C. to give 1.150 g (yield 46.1% based on free alkali content) of phosphate of compound A. Melting range: 205~258° C. (not completely melted).

Example 4 for Preparation

Preparation of Mesylate of Compound A 170 g (0.428 mol) of Compound A, 42.5 g (0.442 mol) of methanesulfonic acid and 2.55 L of 95% aqueous solution of isopropanol were added into a 5 L reaction bottle. The mixture was stirred and heated to be completely dissolved under nitrogen protection and in dark. A light yellow clear solution was obtained, and filtered while hot. After cooling to the room temperature, crystals precipitated from the solution. The resulting precipitates were collected by filtration and washed with isopropanol, dried in vacuum to give 180.2 g (0.365 mol) of white acicular crystals. Yield: 85.4%.

180.2 g of mesylate of compound A in a 2.52 L of 95% aqueous solution of isopropanol was added into a 5 L reaction bottle. The mixture was stirred and heated to completely dissolve under nitrogen protection and in the dark, and filtered while hot. After cooling to the room temperature, crystals precipitated from the solution. The resulting precipitates were collected by filtration and washed with isopropanol, dried in vacuum to give 161.5 g of white acicular crystals. Yield: 85.4%. Melting range: 193.5~195° C.

Example 5 for Preparation

Preparation of Citrate of Compound A 2.886 g of free base of compound A, 0.522 g of citric acid and 80 mL of ethanol were mixed and heated to nearly boiling until a colorless clear solution was obtained. After cooling to the room temperature, white crystals were precipitated and filtered. The filter cake was washed with ethanol (3 mL×2), filtered in a vacuum drying oven for 6 hours at 80° C. to give 2.283 g of acicular crystals. Yield: 79%. Melting range: 160.5~162.0° C.

Example 6 for Preparation

Preparation of Maleate of Compound A 2.508 g of free base of compound A, 0.351 g of maleic acid and 110 mL of ethanol were mixed and heated under reflux until a clear light yellow solution was obtained. The solution was boiled and active carbon was added. A spot of flocculent insoluble matters were removed by hot filtration. The filtrate was concentrated to about 90 mL, and cooled to the room temperature. Light yellow crystalline solids were precipitated and filtered. The filter cake was washed with a small amount of ethanol, filtered in vacuum drying oven for 6 h at 80° C., to give 1.009 g of light yellow acicular crystals. Yield: 40%. Melting range: 115~160° C.

Example 7 for Preparation

Preparation of Succinate of Compound A 2.827 g of free base of compound A, 0.401 g of succinic acid and 70 mL of ethanol were mixed and heated to reflux. The solid matters were completely dissolved. The solution was boiled and active carbon was added. A spot of flocculent insoluble matters were removed by hot filtration. The filtrate was concentrated to about 25 mL, and cooled to the room temperature. White crystalline solids were precipitated and filtrated. The filter cake was washed with a small amount of ethanol, filtered in a vacuum drying oven for 6 hours at 80° C. to give 1.009 g of light yellow acicular crystals. Yield: 77%. Melting range: 117~161.5° C.

2. Properties of Pharmaceutically Acceptable Salts of Compound A

(1) Characters

|  | Character |
|---|---|
| Compound A | Off-white solid |
| Hydrochloride of compound A | Light yellow crystal |
| Maleate of compound A | White acicular crystal |
| Phosphate of compound A | White granular crystal |
| Mesylate of compound A | White bitty acicular crystal |

(2) Melting Points

|  | Melting point |
|---|---|
| Compound A | 158.5~161.5° C. (shriveling from 150° C.) |
| Hydrochloride of compound A | 200~202.5° C. |
| Maleate of compound A | 159.5~160.5° C. (decompose while melting) |
| Sulfate of compound A | 199.5~230° C. (not completely melted) |
| Phosphate of compound A | 205~258° C. (not completely melted) |
| Mesylate of compound A | 193.5~195° C. |

(3) Solubility

|  | Solubility in water | Solubility in ethanol |
|---|---|---|
| Compound A | Insoluble | 0.1 g/23 mL slightly soluble |
| Hydrochloride of compound A | very slightly soluble, with opalescence | 0.1 g/40 mL slightly soluble |
| Maleate of compound A | Insoluble | 0.1 g/25 mL slightly soluble |
| Phosphate of compound A | Insoluble | 0.1 g/49 mL slightly soluble |
| Mesylate of compound A | Insoluble | 0.1 g/20 mL slightly soluble |

(4) Stability

Stability of Different Pharmaceutically Acceptable Salts of Compound A in Different Conditions (Initial purity of materials: 99.6%, content determined by HPLC method)

| | Samples | | | | | | | |
|---|---|---|---|---|---|---|---|---|
| | Compound A | Hydrochloride | Mesylate | Sulfate | Phosphate | Maleate | Citrate | Succinate |
| 6 Months Under Light | 95.2% | 97.6% | 99.5% | 97.6% | 97.1% | 94.2% | 94.8% | 94.2% |
| 6 Months in Relative Humidity of 90% | 94.6% | 97.3% | 98.6% | 94.8% | 95.0% | 96.4% | 95.3% | 94.8% |
| 6 Months at Room Temperature | 95.7% | 98.2% | 99.5% | 98.5% | 97.3% | 96.4% | 96.3% | 96.2% |
| 6 Months at 60° C. | 92.2% | 94.7% | 98.4% | 96.2% | 94.2% | 93.5% | 93.0% | 93.8% |

Conclusion: According to the result of stability experiments, the stability of hydrochloride and mesylate is most satisfying. In particular, mesylate is most stable.

3. Research on Pharmacological Activity of Pharmaceutically Acceptable Salts of Compound A Example 1

Inhibition of Mesylate of Compound A on Receptor Protein Tyrosine Kinase (1) Method ELISA method (I Posner et al., J. Biol. Chem., October, 1992, Vol. 267, Issue 29, 20638-20647): Enzyme label plate was coated with enzyme reaction substrate Poly(Glu, Tyr)$_{4:1}$, then enzyme, sample and ATP were added. Phosphorylation of substrate was determined with monoclonal antibody of anti-phosphorylation tyrosine (PY99). Goat anti-mouse IgG marked with HRP was then added, and the degree of phosphorylation of substrate was determined with OPD coloration. At the same time, the control group without tyrosine kinase and control wells of corresponding DMSO concentration were set up. 2 M of $H_2SO_4$ was added in 50 μl/well to terminate the reaction. Data was read with adjustable wavelength micro plate enzyme-labeling instrument VERSAmax (Sunnyvale, Calif., U.S.A.), followed by visualization reaction, OD490 nm value was then observed.

$$\text{Inhibition rate} = \left(1 - \frac{\text{OD value of compound} - \text{OD value of no enzyme control well}}{\text{OD value of negative control group} - \text{OD value of no enzyme control well}}\right) \times 100\%$$

Relative inhibition rate of drugs on tyrosine kinase protein was determined.

Inhibitory concentration 50% $IC_{50}$ was calculated by LOGIT method according to the inhibition rates of different concentrations. Each above-mentioned experiment was repeated 3 times, and the average $IC_{50}$ value of 3 times of experiments was taken as the final index of inhibition ability.

(2) Results

The results of the inhibition of mesylate of compound A and positive control compound PTK787 on 8 types of tyrosine kinases were summarized in table 1. The results show that mesylate of compound A has a significant inhibition on the kinase activity of KDR, Flt1, PDGFRβ, c-Kit and c-Src in the molecular level, $IC_{50}$ of which are 2.43 nM, 70.08 nM, 537.31 nM, 420.31 nM, and 348.53 nM, respectively. In contrast, $IC_{50}$ of positive control compound PTK787 on KDR, Flt1, PDGFRβ and c-Kit are 33.30 nM, 84.69 nM, 416.51 nM, and 606.11 nM, respectively. The results also show mesylate of compound A has strong inhibition on the kinase activity of vascular endothelial growth factor receptors 1 and 2 (Flt1/VEGFR1 and KDR/VEGFR2). Its inhibition on KDR kinase is significantly stronger than that on Flt1 kinase, and $IC_{50}$ on KDR kinase is 13.7 times lower than that of control compound. That is to say, the inhibition of mesylate of compound A on KDR is stronger than PTK787. Meanwhile, mesylate of compound A also has a considerable inhibition on other third receptor tyrosine kinases, such as platelet-derived growth factor receptor β (PDGFRβ) and stem cell growth factor receptor (c-Kit), which is weaker than its inhibition on vascular endothelial growth factor receptor. When the concentration is increased to $10^4$ nM, positive compound PTK787 has no inhibition on non-receptor tyrosine kinase c-Src, whereas $IC_{50}$ of the inhibition of mesylate of compound A on c-Src is 348.53 nM. However, when the concentration is increased to $10^4$ nM, mesylate of compound A has no inhibition on the kinase activity of kinases from other families, such as epidermal growth factor receptor EGFR1 and ErbB2, and fibroblast growth factor receptor FGFR1. Further, the results show that the inhibition of mesylate of compound A on the kinase activity of KDR is stronger than positive compound PTK787 in the molecular level, while their inhibitions on tyrosine kinase Flt1, PDGFR, c-Kit are essentially the same with inhibition strength ranging in the same level. With regard to selectivity, mesylate of compound A is more extensive than PTK787, and it also has inhibition on the kinase activity of non-receptor tyrosine kinase c-Src. In summary, mesylate of compound A is a tyrosine kinase inhibitor having significantly selective inhibition on KDR, together with inhibition on kinases Flt1, PDGFR, c-Kit, c-Src etc.

TABLE 1

Effects of Mesylate of Compound A on Tyrosine Kinases *

| Kinases | PTK787 ($IC_{50}$ ± SD nM) | Mesylate of compound A ($IC_{50}$ ± SDnM) |
|---|---|---|
| KDR | 33.30 ± 14.45 | 2.43 ± 1.30 |
| Flt1 | 84.69 ± 20.65 | 70.08 ± 29.36 |
| PDGFRβ | 416.51 ± 143.73 | 537.31 ± 190.46 |
| c-Kit | 606.11 ± 77.93 | 420.31 ± 40.37 |
| EGFR1 | >10,000 | >10,000 |
| ErbB2 | >10,000 | >10,000 |
| FGFR1 | >10,000 | >10,000 |
| c-Src | >10,000 | 348.53 ± 194.42 |

Example 2

Efficacy of Mesylate of Compound A on Human Colon Cancer Ls174t Transplanted in Nude Mice (1) Experimental Animals BALB/cA-nude mice, ♀, 5-6 weeks-old, available from Shanghai Slaccas experimental animals limited liability company. Certification number: SCXK (hu) 2004-0005. Rearing environment: SPF grade.

(2) Experimental Procedures

After one week adaption, the experimental animals were subcutaneously inoculated with human colon cancer Ls174t tumor tissues. When the tumors grew to 100-300 mm³, the animals were randomly divided into several groups in day 0 (d0). Doses of mesylate of compound A were 50 mg/kg, 100 mg/kg, and 200 mg/kg, respectively. PTK787 were administered at the same doses. Both mesylate of compound A and PTK787 were orally administered (by gavage) once daily from day 0 (d0) to the 13th day (d13), 14 times in total. The volumes of tumors and the weights of mice were measured 2-3 times every week, the data of which were recorded. The equation for the calculation of volume of tumors (V) is:

$$V = \frac{1}{2} \times a \times b^2$$

wherein a and b represent length and width, respectively.

(3) Results

It has been proved by enzymology and cellular level experiments that the leading action target of mesylate of compound A was VEGFR2/KDR (IC50=2.43±1.30 nM). PTK787 (IC50 on KDR is 33.30±14.45 nM) of Novartis, a compound having similar action target and the clinical trials of which was conducted early, was selected as the positive compound in the experiment. According to the pre-trails of mesylate of compound A and the references (J. M. Wood et al. Cancer Research 60, 2178-2189, Apr. 15, 2000) of PTK787, three dosages of 50, 100, 200 mg/kg were selected, and efficacy evaluation and comparison were conducted using the same doses and dosage regimen. The results are listed in table 2. The results show that mesylate of compound A dose-dependently inhibited the growth of human colon cancer Ls174t, and its T/C % was 16.3% at a dosage of 200 mg/kg. PTK787 also inhibited the growth of Ls174t at a dosage of 200 mg/kg, however, its T/C % was only 60.2%, indicating that the efficacy of PTK787 is significantly inferior to mesylate of compound A. It is reported by J. M. Wood et al. Cancer Research 60, 2178-2189, Apr. 15, 2000, that the best T/C % could reached 40% when PTK787 was administered at a dosage of 75 mg/kg, but the inventors' experimental results showed that PTK787 administered at a dosage of 100 mg/kg has no significant effect, and T/C % was only 71.5%. Upon comparison, it is noted that in J. M. Wood et al.'s experiment, the initial volume of the tumors when the drugs were administered was 25-100 mm3, which was at least 1.5 to 6 folds smaller than that in our experiment, and the administration lasted for 28 days or more, which was longer than that in our experiment. Furthermore, the T/C % reported by J. M. Wood et al. was the best among those in their experiment, but not the final T/C % when the experiment ended. In contrast, the best T/C % in our experiment appeared in 10th day during administration, at that time, T/C % were 60.7% and 45.8% for PTK787 dosage of 100 mg/kg and 200 mg/kg, respectively, which were close to the values in J. M. Wood et al.'s experiment. In addition, it should be emphasized that there are various factors affecting the efficacy of the experiment, comparison should be made in the same system. Although the efficacy of PTK787 in the present experiment was not identical with the literature, the comparison between the efficacy of PTK787 and mesylate of compound A was not affected. It could be calculated from table 2 that ED50 of mesylate of compound A on colon cancer Ls174t was 97.2 mg/kg, whereas ED50 of PTK787 was 458.7 mg/kg, indicating the efficacy of mesylate of compound A on colon cancer Ls174t was significantly better than PTK787.

It should be pointed out that, when mesylate of compound A and PTK787 were both administered at a dosage of 400 mg/kg, their efficacy did not increase significantly although they could be tolerated by mice, i.e. there is no obvious dose-effect relationship. This result was similar to another angiogenesis inhibitor SU11248. Therefore, in the following experiments, the dosages of 200, 100, 50 mg/kg of mesylate of compound A were selected to evaluate the efficacy.

According to the experiment scheme, the two compounds were successively administrated to the tumor-bearing mice for 14 days, respectively. The results show that the two compounds were both well tolerated and there was no obvious weight loss in mice. The toxicity of the two compounds differed little in the experiment scheme.

TABLE 2

Efficacy of Mesylate of Compound A and PTK787 by Oral Administration (p.o) on Human Colon Cancer Ls174t Transplanted in Nude Mice.

| Group | Dose (mg/kg) | Animal Number d0 | dn | Weight after Removing Tumor (g) d0 | Dn | TV x ± SD d0 | dn | RTV x ± SD | T/C (%) |
|---|---|---|---|---|---|---|---|---|---|
| Control | | 12 | 12 | 18.6 | 16.6 | 165 ± 32 | 1978 ± 445 | 12.3 ± 3.4 | |
| Mesylate of Compound A | 50 | 6 | 6 | 19.1 | 16.8 | 155 ± 33 | 1452 ± 149 | 9.8 ± 3.0 | 79.7 |
| Mesylate of Compound A | 100 | 6 | 6 | 19.0 | 18.5 | 161 ± 44 | 931 ± 196 | 6.4 ± 3.1 | 52.0[a] |
| Mesylate of Compound A | 200 | 6 | 6 | 18.6 | 18.5 | 158 ± 20 | 310 ± 114 | 2.0 ± 0.9 | 16.3[a] |
| PTK787 | 50 | 6 | 6 | 19.5 | 17.6 | 171 ± 39 | 1425 ± 613 | 9.4 ± 5.9 | 76.4 |
| PTK787 | 100 | 6 | 6 | 19.3 | 17.3 | 175 ± 43 | 1538 ± 402 | 8.8 ± 3.5 | 71.5 |
| PTK787 | 200 | 6 | 6 | 18.8 | 17.1 | 150 ± 25 | 1076 ± 198 | 7.4 ± 2.0 | 60.2[a,b] | d0: split-cage administration time;
dn: 14 days after the first administration.
[a]$P < 0.01$ vs control;
[b]$P < 0.01$ vs group of mesylate of compound A at a dosage of 200 mg/kg.

Example 3

Efficacy of Mesylate of Compound A on Human Colon Cancer HT-29 Transplanted in Nude Mice (1) Experimental Animals BALB/cA-nude mice, ♀, 5-6 weeks-old, purchased from Shanghai Slaccas experimental animals limited liability company. Certification number: SCXK (Hu) 2004-0005. Rearing environment: SPF grade.

(2) Experimental Procedures

After one week adaption, the experimental animals were subcutaneously inoculated with human colon cancer HT-29 tumor tissues. When the tumors grew to 100-300 mm$^3$, the animals were randomly divided into several groups. Dosages of mesylate of compound A were 50 mg/kg, 100 mg/kg, 200 mg/kg, respectively, and dosage of PTK787 was 200 mg/kg. Both mesylate of compound A and PTK787 were oral administered (by gavage) once daily from d0 to d20, 21 times in total. Volume of tumors and weight of mice were measured 2-3 times every week, the data of which were recorded. The equation for the calculation of volume of tumors (V) is:

$$V = \tfrac{1}{2} \times a \times b^2$$

wherein a, b represent length and width, respectively.

(1) Result (See Table 3)

The results show that mesylate of compound A significantly inhibited the growth of human colon cancer HT-29 with obvious dose-dependency. The efficacy of PTK787 was also good, but inferior than that of mesylate of compound A. T/C % of mesylate of compound A and PTK787 at a dosage of 200 mg/kg were 25.5% and 56.5%, respectively, which differed significantly (P<0.01). This indicates that the efficacy of mesylate of compound A was much better than PTK787. In addition, the two compounds were both well tolerated and the toxicities were equivalent.

TABLE 3

Efficacy of Mesylate of Compound A and PTK787 by Oral Administration (p.o) on Human Colon Cancer HT-29 Transplanted in Nude Mice.

| Group | Dosage (mg/kg) | Animal Number | | Weight after Removing Tumor (g) | | TV x ± SD | | RTV x ± SD | T/C (%) |
|---|---|---|---|---|---|---|---|---|---|
| | | d0 | dn | d0 | dn | d0 | dn | | |
| Control | | 12 | 12 | 16.8 | 14.1 | 229 ± 38 | 1945 ± 499 | 8.67 ± 2.41 | |
| Mesylate of compound A | 50 | 6 | 6 | 16.1 | 14.3 | 239 ± 49 | 1250 ± 256 | 5.42 ± 1.55 | 62.5 |
| Mesylate of compound A | 100 | 6 | 6 | 17.0 | 16.4 | 272 ± 37 | 998 ± 296 | 3.78 ± 1.46 | 43.6[a] |
| Mesylate of compound A | 200 | 6 | 6 | 16.3 | 15.6 | 260 ± 39 | 571 ± 147 | 2.21 ± 0.52 | 25.5[a] |
| PTK787 | 200 | 6 | 6 | 15.9 | 13.9 | 252 ± 43 | 1185 ± 143 | 4.9 ± 1.36 | 56.5[a,b] | d0: split-cage administration time;
dn: 21 days after the first administration.
[a]P < 0.01 vs control;
[b]P < 0.01 vs group of mesylate of compound A at a dosage of 200 mg/kg.

Example 4

Research on Bioavailability of Compound A by Oral Administration (1) Experimental Animals Male Sprague-Dawley (SD) rats (weight: about 250 g, experimental animal certification of fitness: 0006473) were purchased from Shanghai Slaccas experimental animals limited liability company (certification number: SCXK (hu) 2003-0003). The relevant qualifications and state of health of the SD rats were checked first, and the eligible were placed into the clean grade rats chambers in Shanghai institute of materia medica.

(2) Experimental Instruments

Liquid chromatography-mass spectrometry analysis system (LC/MS/MS) includes an Agilent1100 series binary pump, an online deaerator, an autosampler, column heaters, and a TSQ Quantum triple quadrupole mass spectrometer from Thermo Finnigan Company. Working softwares of the system are Xcalibur and Chemstation (America). Other experimental instruments include: a Techne nitrogen drying apparatus (German); a −80° C. ultra low temperature SANYO freezer (Japan); a Vibrax VXR miniature shaker (German); a MS1 turbine mixer (German); a 92-2 Timing Stable Temperature Magnetic Stirrer (Shanghai); a METTLER AE240 double range electronic analytical balance (0.01 mg/41 g, 0.1 mg/205 g) (German); and EPPENDORF continuous liquid filler (German).

(3) Experimental Methods

I. Analysis Condition of LC/MS/MS
Analysis Condition of Liquid Chromatography
Chromatographic column: Agilent Zorbax SB-C18 column (50 mm×2.1 mm ID);
Column temperature: 25° C.;
Mobile phase: A: $H_2O$—$CH_3CN$ (2:98, v/v), B: $H_2O$—$CH_3CN$ (10:90, v/v)
A: 25%+B: 75%, constant gradient elution;
Flow rate: 0.25 mL/min;
Injection volume: 10 µL;
Analysis time: 3 minutes.

II. Experiments with Rats

The light circle was switched to 12/12 hour day/night in the clean grade chambers of rats. Humidity and temperature were 40-60% and 20-24° C., respectively. Every 4 rats were raised in a 36×24×19 $cm^3$ stainless rat cage. The rats took water freely and were fed special rat food regularly once daily. Only after one week adaption, the rats could be used to conduct pharmacokinetics animal experiment. 3 Sprague-Dawley rats were orally administered compound A at a dosage of 20 mg/kg.

24 mg of compound A powder was precisely weighed, dissolved in 4 mL of water, placed in a mortar and grounded, and then flushed with 8 mL of water into a 15 mL test tube to give a 2 mg/mL suspension for animal experiments.

The blood samples were collected 0 hour before the administration and 0.083, 0.25, 0.5, 1.0, 2, 4, 6, 8 hours after the administration. 250~300 µL of the blood samples of rats were collected at each time point from posterior venous sinus of the eyes after respiration anaesthesia with ether (the degree of anaesthesia was highly controlled). The blood samples were collected into test tubes containing heparin added in advance, and then centrifuged to produce plasma. The obtained plasma was divided into 2 parts (50 µL for each part) and stored at −70° C. until analysis. The concentrations of compound A in blood samples at different time points were analyzed using LC/MS/MS method. Euthanasia was performed on used rats with $CO_2$ gas.

Pharmacokinetics parameters of animal experiment of each group were calculated using InnaPhase Kinetica™ software (America).

III. Results of Experiments

TABLE 4

Pharmacokinetics Parameters of SD Rats after Oral Administration of Compound A (20 mg/kg) (Non-compartment Model)

|  | Rat 1 | Rat 2 | Rat 3 | Mean ± SD |
|---|---|---|---|---|
| Cmax (ng/mL) | 60.8 | 68.9 | 79.2 | 69.6 ± 9.2 |
| Tmax (h) | 1.5 | 1.5 | 1 | 1.33 ± 0.29 |
| $AUC_{0 \to 8h}$ (ng·h/mL) | 172 | 295 | 211 | 226 ± 63 |
| $T_{1/2}$(h) | 2.13 | 1.12 | 2.09 | 1.78 ± 0.57 |
| $K_{el}$ (h$^{-1}$) | 0.325 | 0.622 | 0.332 | 0.426 ± 0.169 |
| MRT (h) | 3.20 | 3.38 | 3.32 | 3.30 ± 0.09 |
| CL (L/h/kg) | 115 | 67.4 | 92.7 | 91.5 ± 23.6 |
| Vd (L/kg) | 366 | 228 | 308 | 300 ± 69.4 |

*Cmax: the maximum plasma drug concentration after the extravascular administration;
Tmax: extravascular administration time;
$AUC_{0-8h}$: plasma drug concentration-time area under curve (0 to 8th hour);
$T_{1/2}$: half life;
$K_{el}$: the elimination rate constant;
MRT: the mean retention time in vivo of a single molecule;
CL: the plasma clearance;
Vd: apparent distribution volume based on the plasma concentration.

Example 5

Comparison Between Bioavailabilities of Four Pharmaceutically Acceptable Salts of Compound A by Oral Administration (1) Experimental Animals Male Sprague-Dawley (SD) rats (weight: about 250 g, experimental animal certification of fitness: 0006473) were purchased from Shanghai Slaccas experimental animals limited liability company (certification number: SCXK (Hu) 2003-0003). The relevant qualifications and state of health of the SD rats were checked first, and the eligible ones were placed into the clean grade chambers of rats in Shanghai institute of Materia Medica.

(2) Experimental Instruments

Liquid chromatography-mass spectrometry analysis system (LC/MS/MS) includes an Agilent 1100 series binary pump, an online deaerator, an autosampler, column heaters, and a TSQ Quantum triple quadrupole mass spectrometer from Thermo Finnigan company. Working softwares of the system are Xcalibur and Chemstation (America). Other experimental instruments include: a Techne nitrogen drying apparatus (German); a −80° C. ultra low temperature SANYO freezer (Japan); a Vibrax VXR miniature shaker (German); a MS1 turbine mixer (German); a 92-2 Timing Stable Temperature Magnetic Stirrer (Shanghai); a METTLER AE240 double range electronic analytical balance (0.01 mg/41 g, 0.1 mg/205 g) (German); and an EPPENDORF continuous liquid filler (German).

(3) Experimental Methods

I. Analysis Condition of LC/MS/MS
Analysis Condition of Liquid Chromatography
Chromatographic column: Agilent Zorbax SB-C18 column (50 mm×2.1 mm ID);
Column temperature: 25° C.;
Mobile phase: A: $H_2O$—$CH_3CN$ (2:98, v/v), B: $H_2O$—$CH_3CN$ (10:90, v/v)
A: 25%+B: 75%, constant gradient elution;
Flow rate: 0.25 mL/min;
Injection volume: 10 μL;
Analysis time: 3 minutes.

II. Experiments with Rats

The light circle was switched to 12/12 hour day/night in the clean grade chambers of rats. Humidity and temperature were 40-60% and 20-24° C., respectively. Every 4 rats were raised in a 36×24×19 cm$^3$ stainless rat cage. The rats took water freely and were fed special rat food regularly once daily. Only after one week adaption, the rats were used to conduct pharmacokinetics studies. 12 Sprague-Dawley rats were divided into 4 groups, 3 for each group. The four groups were orally administered hydrochloride, phosphate, maleate and mesylate of compound A at a dosage of 20 mg/kg, respectively.

24 mg powder of hydrochloride, phosphate, maleate and mesylate of compound A were precisely weighed respectively, dissolved in 4 mL of water, placed in mortars and grounded, and then flushed with 8 mL of water into 15 mL test tubes to give a 2 mg/mL suspensions for animal experiments.

The blood samples were collected 0 hour before the administration and 0.083, 0.25, 0.5, 1.0, 2, 4, 6, and 8 hours after the administration. The blood samples were collected at 250~300 μL at each time point from posterior venous sinus of the eye after respiration anaesthesia with ether (the degree of anaesthesia was highly controlled). The blood was collected into test tubes containing heparin, and then was centrifuged to produce plasma. The obtained plasma was divided into 2 parts (50 μL for each part) and stored at −70° C. until analysis. The concentrations of compound A in blood samples at different time points were analyzed with LC/MS/MS methods. After experiments, euthanasia was performed with $CO_2$ gas.

Pharmacokinetics parameters of animal experiment of each group were calculated using InnaPhase Kinetica™ software (America).

III. Results of Animal Experiments

Figure 3:
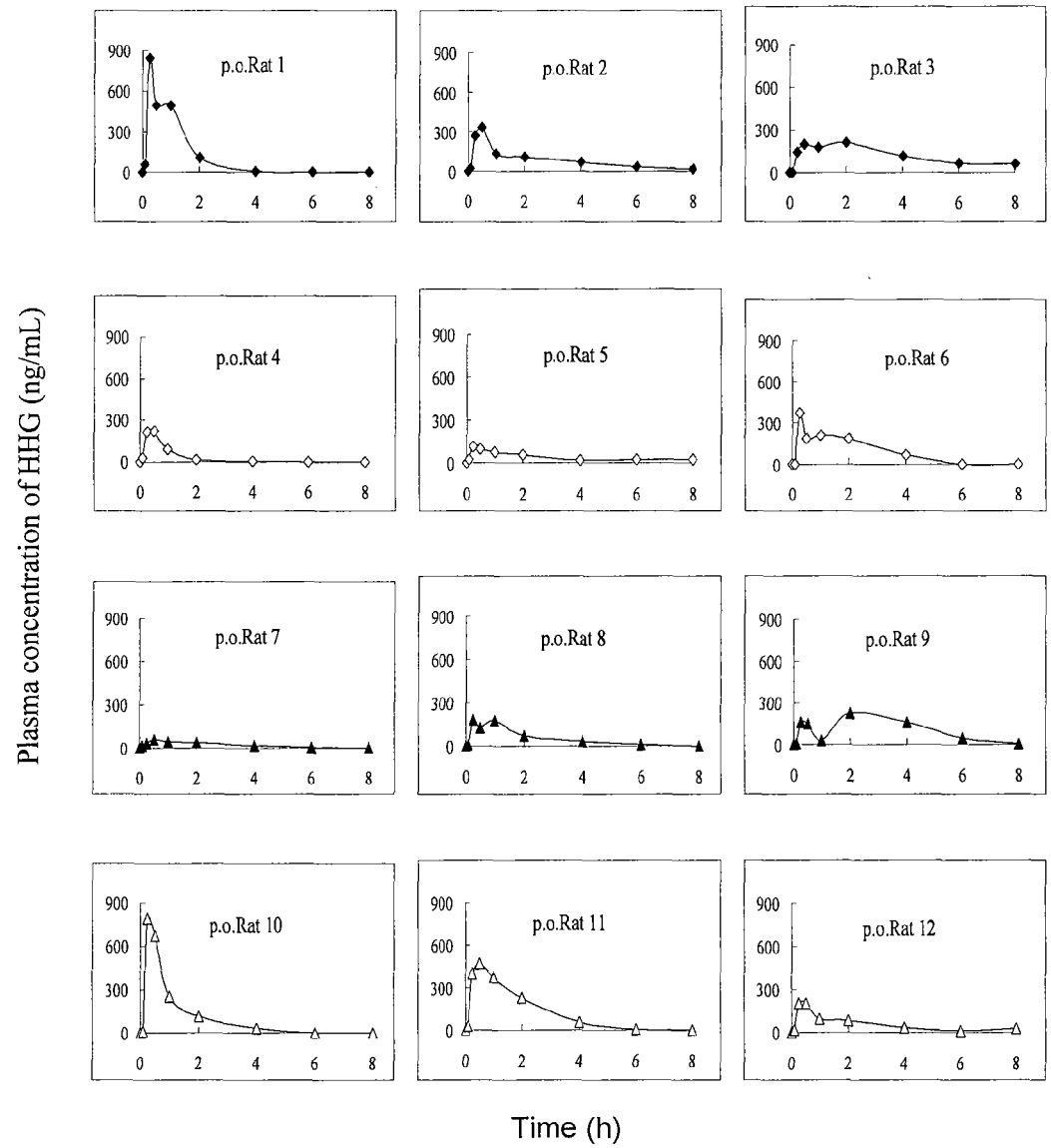
FIG. 3: Drug concentration-time curve of hydrochloride (Rat 1~3), phosphate (Rat 4~6), maleate (Rat 7~9) and mesylate (Rat 10~12) of compound A of 20 mg/kg orally administered to rats.

Blood concentrations of hydrochloride, phosphate, maleate and mesylate of compound A orally administered at a dosage of 20 mg/kg to rats at different time points, are listed in tables 5 and 6, respectively. Corresponding plasma drug concentration-time curves are shown in FIG. 3, and pharmacokinetics parameters are listed in tables 7 and 8.

TABLE 5

Blood Concentrations of Compound A in Rats at Different Time Points after Oral Administration of Hydrochloride and Phosphate of Compound A at a Dosage of 20 mg/kg

| Time of Blood Taking (h) | Blood Concentration (ng/mL) | | | | | |
|---|---|---|---|---|---|---|
| | Hydrochloride | | | Phosphate | | |
| | Rat 1 | Rat 2 | Rat 3 | Rat 4 | Rat 5 | Rat 6 |
| 0 | 0 | 0 | 0 | 0 | 0 | 0 |
| 0.083 | 54.6 | 21.6 | ND | 30.6 | 23.3 | 1.88 |
| 0.25 | 843 | 270 | 142 | 218 | 115 | 375 |
| 0.5 | 491 | 336 | 199 | 222 | 95.0 | 188 |
| 1 | 493 | 133 | 179 | 92.8 | 73.9 | 212 |
| 2 | 110 | 111 | 212 | 19.8 | 56.4 | 184 |
| 4 | 2.90 | 71.8 | 114 | 5.88 | 19.1 | 67.8 |
| 6 | 1.88 | 38.2 | 65.2 | 0.144 | 22.0 | 0.735 |
| 8 | ND | 15.9 | 60.4 | 0.421 | 24.7 | ND |

TABLE 6

Blood Concentrations of Compound A in Rats at Different Time Points after Oral Administration of Maleate and Mesylate of Compound A at a Dosage of 20 mg/kg

| Time of Blood Taking (h) | Blood concentration (ng/mL) | | | | | |
|---|---|---|---|---|---|---|
| | Maleate | | | Mesylate | | |
| | Rat 7 | Rat 8 | Rat 9 | Rat 10 | Rat 11 | Rat 12 |
| 0 | 0 | 0 | 0 | 0 | 0 | 0 |
| 0.083 | 18.0 | 12.2 | 3.79 | 13.2 | 26.9 | 15.7 |
| 0.25 | 33.9 | 186 | 164 | 794 | 400 | 204 |
| 0.5 | 59.7 | 126 | 149 | 672 | 469 | 203 |
| 1 | 44.8 | 176 | 27.1 | 252 | 370 | 94.4 |
| 2 | 36.0 | 74.0 | 224 | 116 | 228 | 86.9 |
| 4 | 14.0 | 30.7 | 164 | 30.5 | 54.6 | 33.5 |
| 6 | 5.12 | 8.49 | 46.1 | 0.907 | 3.24 | 8.65 |
| 8 | 0.462 | 0.775 | 3.67 | ND | ND | 29.9 |

TABLE 7

Pharmacokinetics Parameters of Compound A in Rats after Oral Administration of Hydrochloride and Phosphate of Compound A at a Single Dosage (20 mg/kg) (Non-compartment Model Analysis)

| Pharmacokinetics Parameters | Hydrochloride | | | | Phosphate | | | |
|---|---|---|---|---|---|---|---|---|
| | Rat 1 | Rat 2 | Rat 3 | Mean ± SD | Rat 4 | Rat 5 | Rat 6 | Mean ± SD |
| $C_{max}$ (ng/mL) | 843 | 336 | 212 | 463 ± 334 | 221.71 | 114.55 | 375.42 | 237 ± 131 |
| $T_{max}$ (h) | 0.25 | 0.50 | 2.00 | 0.92 ± 0.95 | 0.50 | 0.25 | 0.25 | 0.33 ± 0.14 |
| $AUC_{0 \to 8 h}$ (ng · h/mL) | 805 | 669 | 967 | 814 ± 149 | 224.83 | 214.30 | 659.67 | 366 ± 254 |
| $T_{1/2}$ (h) | 0.70 | 1.98 | 3.20 | 1.96 ± 1.25 | 0.81 | 1.51 | 0.75 | 1.02 ± 0.43 |
| $K_{el}$ (h$^{-1}$) | 0.99 | 0.35 | 0.16 | 0.50 ± 0.43 | 0.86 | 0.46 | 0.92 | 0.75 ± 0.25 |
| MRT (h) | 0.98 | 3.08 | 6.24 | 3.43 ± 2.64 | 1.01 | 2.34 | 1.83 | 1.73 ± 0.67 |
| CL (L/h/kg) | 24.8 | 27.9 | 15.0 | 22.6 ± 6.7 | 88.9 | 77.6 | 30.2 | 65.6 ± 31.1 |
| $V_d$ (L/kg) | 24.4 | 85.9 | 93.5 | 67.9 ± 37.9 | 89.8 | 181.3 | 55.3 | 108.8 ± 65.1 |

$C_{max}$: the maximum plasma drug concentration after extravascular administration;
$T_{max}$: the time needed to reach the maximum plasma drug concentration after extravascular administration;
$AUC_{0 \to 8 h}$: plasma drug concentration-time area under curve (0 to 8 h);
$AUMC_{0 \to 8 h}$: first moment-time area under curve (0 to 8 hours);
$T_{1/2}$: half life;
$K_{el}$: elimination rate constant;
MRT: mean retention time in vivo of a single molecule;
CL: plasma clearance;
Vd: apparent distribution volume based on the plasma concentration.

TABLE 8

Pharmacokinetics Parameters of Compound A in Rats after Oral Administration of Maleate and Mesylate of Compound A at a Single Dosage (20 mg/kg) (Non-compartment Model Analysis)

| Pharmacokinetics Parameters | Maleate | | | | Mesylate | | | |
|---|---|---|---|---|---|---|---|---|
| | Rat 7 | Rat 8 | Rat 9 | Mean ± SD | Rat 10 | Rat 11 | Rat 12 | Mean ± SD |
| $C_{max}$ (ng/mL) | 59.68 | 186.39 | 224.42 | 156 ± 86 | 794.42 | 468.62 | 203.86 | 489 ± 296 |
| $T_{max}$ (h) | 0.50 | 0.25 | 2.00 | 0.92 ± 0.94 | 0.25 | 0.50 | 0.25 | 0.33 ± 0.14 |
| $AUC_{0 \to 8 h}$ (ng · h/mL) | 151.13 | 388.28 | 827.22 | 456 ± 343 | 784.11 | 925.94 | 380.10 | 697 ± 283 |
| $T_{1/2}$ (h) | 0.81 | 0.75 | 0.73 | 0.77 ± 0.04 | 0.63 | 0.65 | 1.32 | 0.87 ± 0.39 |
| $K_{el}$ (h$^{-1}$) | 0.85 | 0.92 | 0.95 | 0.91 ± 0.05 | 1.10 | 1.06 | 0.53 | 0.90 ± 0.32 |
| MRT (h) | 2.20 | 1.91 | 3.09 | 2.40 ± 0.61 | 1.18 | 1.61 | 2.13 | 1.64 ± 0.48 |
| CL (L/h/kg) | 131.7 | 51.4 | 24.0 | 69.1 ± 56 | 25.5 | 21.5 | 50.2 | 32.4 ± 15.5 |
| $V_d$ (L/kg) | 290.2 | 98.3 | 74.3 | 154.2 ± 118.3 | 30.1 | 34.7 | 107.0 | 57.3 ± 43.2 |

$C_{max}$: the maximum plasma drug concentration after extravascular administration;
$T_{max}$: the time needed to reach the maximum plasma drug concentration after extravascular administration;
$AUC_{0 \to 8 h}$: plasma drug concentration-time area under curve (0 to 8 hours);
$AUMC_{0 \to 8 h}$: first moment-time area under curve (0 to 8 hours);
$T_{1/2}$: half life;
$K_{el}$: elimination rate constant;
MRT: mean retention time in vivo of a single molecule;
CL: plasma clearance;
Vd: apparent distribution volume based on the plasma concentration.

TABLE 9

Relative Bioavailability of Oral Administration of Pharmaceutically Acceptable Salts of Compound A in the Experiment

|  | Hydrochloride | Phosphate | Maleate | Mesylate |
| --- | --- | --- | --- | --- |
| MW | 433.93 | 495.47 | 513.54 | 493.58 |
| Dose (mg/kg) | | | 20 | |
| Mol dose (μmol/kg) | 46 | 40 | 39 | 41 |
| $C_{max}$ (ng/mL) | 463 ± 334 | 237 ± 131 | 156 ± 86 | 489 ± 296 |
| $T_{max}$ (h) | 0.92 ± 0.95 | 0.33 ± 0.14 | 0.92 ± 0.94 | 0.33 ± 0.14 |
| $AUC_{0 \to 8\,h}$ (ng·h/mL) | 814 ± 149 | 366 ± 254 | 456 ± 343 | 697 ± 283 |
| $AUC_{0 \to 8\,h}$ Mol dose (ng·h/mL) | 17653 ± 3232 | 9074 ± 6292 | 11697 ± 8807 | 17194 ± 6984 |
| Relative F | hydrochloride > mesylate > maleate > phosphate | | | |

*Cmax: the maximum plasma drug concentration after extravascular administration; Tmax: the time needed to reach the maximum plasma drug concentration after extravascular administration; AUC(0→8 h): plasma drug concentration-time area under curve (0 to 8 hours); $AUC_{0 \to 8\,h}$ Mol dose (ng·h/mL): plasma drug concentration-time area under curve (0 to 8 hours) at a dosage of 1 mmol/kg; Relative F: relative bioavailability.

Conclusion: compared with the bioavailability of compound A determined in example 4, it was found that the salts of compound A in the present invention greatly improved the bioavailability of compound A, especially the hydrochloride and mesylate of compound A.

4. Formulation

Preparation Example 1

Tablet

Prescription

| Mesylate of compound A | 100 g |
| --- | --- |
| Starch | 20 g |
| 2% starch slurry | appropriate amount |
| Magnesium stearate | 0.5 g |
| | 1000 tables |

Preparation process: Pharmaceutically acceptable salts of compound A were sieved through a 100~200 mesh sieve, and mixed with starch. 2% starch slurry was added, and the mixture was granulated, dried, and mixed with magnesium stearate. The resulting mixture was compressed and tested. The eligible one was packaged.

Preparation Example 2

Capsule

Prescription

| Mesylate of compound A | 50 g |
| --- | --- |
| Starch | 10 g |
| Microcrystalline cellulose | 5 g |
| 1% starch slurry | appropriate amount |
| Magnesium stearate | 0.25 g |
| | 1000 capsules |

Preparation process: The mixture was granulated, encapsulated, tested and packaged in a conventional way.

What is claimed is:

1. A mesylate salt of N-[4-(1-cyanocyclopentyl)phenyl]-2-(4-pyridylmethyl)amino-3-pyridine carboxamide.

2. A pharmaceutical composition comprising a therapeutically effective amount of a salt of claim 1, and at least one pharmaceutically acceptable carrier.

3. A process for the preparation of a mesylate salt of N-[4-(1-cyanocyclopentyl)phenyl]-2-(4-pyridylmethyl)amino-3-pyridine carboxamide, comprising the step of contacting N-[4-(1-cyanocyclopentyl)phenyl]-2-(4-pyridylmethyl) amino-3-pyridine carboxamide with methansulfonic acid.

4. A method of treating colon cancer comprising administering a mesylate salt of N-[4-(1-cyanocyclopentyl)phenyl]-2-(4-pyridylmethyl)amino-3-pyridine carboxamide.

* * * * *